United States Patent
Swoboda et al.

(10) Patent No.: US 8,894,584 B2
(45) Date of Patent: Nov. 25, 2014

(54) REAL TIME CSF FLOW MEASUREMENT SYSTEM AND METHOD

(75) Inventors: Marek Swoboda, Philadelphia, PA (US); Matias Gabriel Hochman, Philadelphia, PA (US); Mark Evan Mattiucci, Newtown Square, PA (US); Frederick J. Fritz, Skillman, NJ (US)

(73) Assignee: Shuntcheck, Inc., Bensalem, PA (US)

( * ) Notice: Subject to any disclaimer, the term of this patent is extended or adjusted under 35 U.S.C. 154(b) by 145 days.

(21) Appl. No.: 13/698,689

(22) PCT Filed: May 27, 2011

(86) PCT No.: PCT/US2011/038317
§ 371 (c)(1),
(2), (4) Date: Dec. 27, 2012

(87) PCT Pub. No.: WO2011/150323
PCT Pub. Date: Dec. 1, 2011

(65) Prior Publication Data
US 2013/0109998 A1    May 2, 2013

Related U.S. Application Data

(60) Provisional application No. 61/396,436, filed on May 28, 2010.

(51) Int. Cl.
*A61B 5/01* (2006.01)
*A61B 5/03* (2006.01)
*A61M 5/168* (2006.01)
*G01F 1/684* (2006.01)

(52) U.S. Cl.
CPC . *A61B 5/032* (2013.01); *A61B 5/01* (2013.01); *A61B 5/031* (2013.01); *A61M 5/168* (2013.01); *A61M 5/16836* (2013.01); *G01F 1/684* (2013.01)
USPC .............................................. 600/549; 604/8

(58) Field of Classification Search
CPC .......... A61B 5/01; A61B 5/031; A61B 5/032; G01F 1/684; G01F 1/688
USPC ........................................... 600/549; 604/8, 9
See application file for complete search history.

(56) References Cited

U.S. PATENT DOCUMENTS 4,548,516 A    10/1985  Helenowski
7,520,862 B2 *  4/2009  Neff .............................. 600/549
(Continued)

FOREIGN PATENT DOCUMENTS

WO    2009146075 A1    12/2009

OTHER PUBLICATIONS

International Search Report for PCT/US2011/038317, Feb. 2012.

*Primary Examiner* — Sean Dougherty
*Assistant Examiner* — Michael C Stout
(74) *Attorney, Agent, or Firm* — Caesar, Rivise, Berntein, Cohen & Polotilow, Ltd.

(57) ABSTRACT

A system for measuring quantitative CSF flow in shunt tubing implanted under the skin. The system includes an array of thermosensors clustered in three sections, cooling device, placed on the skin surface and an associated data acquisition and analysis device. Two sensor sections are placed over the shunt on the skin and measure real time temperature responses related to CSF movement. One array placed adjacent the cooling device collects data on thermal properties of skin including skin thermal condictivity, specific heat, diffusivity, perfusion, and thermal inertia. The method involves assessing thermal properties of skin and measuring CSF flow in shunt tubing. The method is useful for shunt patency assessment, CSF valve adjustment procedures and CSF flow measurements related to CSF over drainage. Alternatively, only one section of sensors need be used when determining relative CSF flow, without the need to determine thermal skin properties and by applying the cooling device continuously.

26 Claims, 10 Drawing Sheets

(56) References Cited

U.S. PATENT DOCUMENTS

| | | | |
|---|---|---|---|
| 8,075,470 B2 * | 12/2011 | Alekseyenko et al. | 600/13 |
| 8,302,471 B2 * | 11/2012 | Van Der Wiel | 73/204.11 |
| 2002/0121137 A1 * | 9/2002 | Fujiwara et al. | 73/204.26 |
| 2004/0068201 A1 | 4/2004 | Saul | |
| 2005/0094707 A1 * | 5/2005 | Lee et al. | 374/163 |
| 2005/0149170 A1 * | 7/2005 | Tassel et al. | 623/1.15 |
| 2005/0171452 A1 * | 8/2005 | Neff | 600/549 |
| 2005/0204811 A1 * | 9/2005 | Neff | 73/204.11 |
| 2006/0000271 A1 * | 1/2006 | Bork | 73/204.26 |
| 2007/0073132 A1 * | 3/2007 | Vosch | 600/393 |
| 2007/0206655 A1 * | 9/2007 | Haslett et al. | 374/141 |
| 2007/0282218 A1 * | 12/2007 | Yarden | 600/549 |
| 2008/0039739 A1 * | 2/2008 | Buja | 600/549 |
| 2008/0150682 A1 * | 6/2008 | Shii | 340/5.22 |
| 2008/0207984 A1 * | 8/2008 | Alekseyenko et al. | 600/9 |
| 2008/0214951 A1 * | 9/2008 | Fritz et al. | 600/549 |
| 2011/0054382 A1 * | 3/2011 | Fritz et al. | 604/9 |

* cited by examiner

REAL TIME CSF FLOW MEASUREMENT SYSTEM AND METHOD

CROSS-REFERENCE TO RELATED APPLICATIONS

This PCT application claims the benefit under 35 U.S.C. §119(e) of Provisional Application Ser. No. 61/396,436 filed on May 28, 2010 entitled REAL TIME CSF FLOW MEASUREMENT SYSTEM AND METHOD and whose entire disclosure is incorporated by reference herein.

STATEMENT REGARDING FEDERALLY SPONSORED RESEARCH OR DEVELOPMENT

This invention was made with government support under R43NS074486 and R44NS074486 awarded by the National Institutes of Health. The government has certain rights in the invention.

BACKGROUND OF THE INVENTION

1. Field of Invention

This present invention generally relates to cerebrospinal fluid (CSF) shunts and, more particular, to a device and method for testing for the presence, absence and/or rate of flow in the shunt tubing implanted under the skin.

2. Description of Related Art

Approximately 69,000 people are diagnosed with hydrocephalus each year in the United States [1]. There are approximately 300,000 shunted hydrocephalus patients in the US [3][4].

The one-year shunt failure rate of shunts is approximately 40% [15, 16], and the mean period to failure is typically only 5-10 years [17]. Obstruction of the ventricular catheter is overwhelmingly the greatest cause [4, 15, 18-20]. Since catheter replacement requires surgery, a need for shunt revision must be reasonably established. Hydrocephalus is a condition of CSF dysregulation, resulting in accumulation of fluid in the brain ventricles. It can lead to neurodegeneration and death if untreated. It is most commonly treated by diverting CSF to the peritoneal cavity by means of a permanent prosthetic shunt.

The usual clinical manifestations of shunt failure (headaches, vomiting) are non-specific, making shunt obstruction difficult to differentiate from less serious illnesses, particularly in pediatric patients in whom three false alarms are seen for every true malfunction [4]. Physical examination, including pumping of the shunt reservoir, is unreliable [21]. CT (computed tomography) remains the gold standard [4, 9], however advanced imaging techniques produce static results, are expensive and cannot be used to investigate every headache, and result in repeated radiological exposures of patients (often children). Current dynamic measures of shunt flow generate only bivariate analyses of "flow" or "no flow" (FIG. 7). New technologies under development are complex (ultrasound tracking of bubbles), lacking in precision (FLIR) or require implantation (implanted thermal flow technologies) and have not reached the clinic.

Thus, there remains a need for a device capable of determining absolute CSF flow rate which has two clinically important applications that are not possible with imaging or bivariate flow measures: (1) prediction of impending catastrophic shunt failure, i.e., monitoring shunt flow in routine examinations enables early recognition of a diminishing flow rate trend in a failing shunt and pre-emption of catastrophic failure; and (2) monitoring and adjusting shunt valve settings to accommodate individual needs for CSF drainage. The degree of impairment in draining CSF varies from hydrocephalic patient to patient. Adjustable shunt valves avoid under drainage and over drainage by the shunt. While the settings for these valves in each patient must currently be determined empirically over a number of weeks, the invention of the present application provides guidance to neurosurgeons and quicker stabilization of CSF homeostasis. In addition to these clinical applications, the shunt flow detection device developed here provides an important research tool for CSF flow behavior in hydrocephalus patients.

All references cited herein are incorporated herein by reference in their entireties.

BRIEF SUMMARY OF THE INVENTION

An apparatus for determining cerebrospinal fluid (CSF) flow rate in an implanted CSF shunt is disclosed. The apparatus comprises: a pad that is placed against the skin of a patient over the location of the CSF shunt wherein the said pad comprises: a first plurality of temperature sensors (e.g., thermistors) that are aligned in a transverse direction with respect to the CSF shunt and wherein one of the first plurality of temperature sensors is aligned with the CSF shunt; and a second plurality of temperature sensors that are aligned in a transverse direction with respect to the CSF shunt, downstream of the first plurality of temperature sensors, and wherein one of the second plurality of temperature sensors is aligned with the CSF shunt; and a third plurality of temperature sensors associated with a temperature source (e.g., a Peltier device, an ice cube, etc.) that positioned over the CSF shunt whenever the pad is placed against the skin; and a sensor processing device that is electrically coupled to the pad for receiving temperature data from each of the plurality of temperature sensors, and wherein the sensor processing device uses the temperature data to remove the effects of skin depth of CSF implantation, skin thermal conductivity and skin thermal diffusivity from temperature data collected by the first, second and third pluralities of temperature sensors, and for determining a flow rate of the CSF through the CSF shunt when a temperature source is applied to the pad.

A method for determining cerebrospinal fluid (CSF) flow rate in an implanted CSF shunt is disclosed. The method comprises: applying a first plurality of temperature sensors against the skin over the location of the CSF shunt and wherein only one of the first plurality of temperature sensors (e.g., thermistors) is aligned with the CSF shunt; applying a second plurality of temperature sensors against the skin over the location of the CSF shunt, downstream of the first plurality of temperature sensors, and wherein only one of the second plurality of temperature sensors is aligned with the CSF shunt; associating a third plurality of temperature sensors with a temperature source (e.g., a Peltier device, an ice cube, etc.), wherein the temperature source being applied against the skin is aligned with the CSF shunt; collecting temperature data from the first, second and third plurality of temperature sensors after a predetermined period of time has elapsed; removing the effects of skin depth of CSF implantation, skin thermal conductivity and skin thermal diffusivity; and determining a flow rate of the CSF through the CSF shunt from the temperature data.

An apparatus for determining intracranial pressure (ICP) of patient having an implanted cerebrospinal fluid (CSF) shunt with an adjustable shunt valve (e.g., a Codman Hakim programmable valve) is disclosed. The apparatus comprises: a pad comprising a plurality of temperature sensors (e.g., thermistors) and a temperature source, said pad being adaptable to be secured to the skin of the patient over a portion of the implanted CSF, and wherein the plurality of temperature sensors detects the movement of a temperature pulse introduced into the CSF of the CSF shunt; a sensor processing device that is electrically coupled to the pad for receiving temperature data from each of the plurality of temperature sensors and for displaying a CSF flow or no CSF flow condition to an operator; and a remote controller for adjusting the adjustable shunt valve; and wherein an operator of the apparatus monitors the sensor processing device to determine if there is or is not any CSF flow and wherein the operator uses the remote controller to change an opening valve pressure of the adjustable shunt valve from an existing valve pressure to a known opening pressure to either initiate a CSF flow that did not previously exist; or to stop an existing CSF flow; and from either of these scenarios determine the ICP based upon the known opening pressure.

A method for determining intracranial pressure (ICP) of a patient having an implanted cerebrospinal fluid (CSF) shunt with an adjustable shunt valve (e.g., a Codman Hakim programmable valve) is disclosed. The method comprises: positioning a plurality of temperature sensor arrays (e.g., thermistors) that can detect the passage of a temperature change experienced by the CSF passing in said CSF shunt and a temperature source (e.g., a Peltier device, an ice cube, etc.), against the skin of a patient over the location of the CSF shunt; analyzing temperature data collected by the plurality of temperature sensors arrays to determine if there is any CSF flow in the CSF shunt or not, wherein the flow-no flow status is visible to a user; adjusting the adjustable shunt valve to change an opening valve pressure from an existing valve pressure to a known opening valve pressure to either initiate a CSF flow that did not previously exist; or to stop an existing CSF flow; and determining the ICP based upon the known opening valve pressure.

An apparatus for controlling cerebrospinal fluid (CSF) flow in an implanted CSF shunt having an adjustable shunt valve (e.g., a Codman Hakim programmable valve) is disclosed. The apparatus comprises: a pad comprising a plurality of temperature sensors (e.g., thermistors) and a temperature source, wherein the pad is adaptable to be secured to the skin of the patient over a portion of the implanted CSF, and wherein the plurality of temperature sensors detects the movement of a temperature pulse introduced into the CSF of the CSF shunt; a sensor processing device that is electrically coupled to the pad for receiving temperature data from each of the plurality of temperature sensors and for displaying a CSF flow or no CSF flow condition to an operator; and a remote controller for adjusting the adjustable shunt valve; and wherein an operator of the apparatus monitors the sensor processing device to determine a flow rate of the CSF in the CSF shunt and then uses the remote controller to change an opening valve pressure of the adjustable shunt valve to achieve a desired CSF flow rate.

A method for controlling cerebrospinal fluid (CSF) flow in an implanted CSF shunt having an adjustable shunt valve (e.g., a Codman Hakim programmable valve) is disclosed. The method comprises: positioning a plurality of temperature sensor arrays (e.g., thermistors) that can detect the passage of a temperature change experienced by the CSF passing in the CSF shunt and a temperature source, against the skin of a patient over the location of the CSF shunt; analyzing temperature data collected by the plurality of temperature sensors arrays to inform a user of a CSF flow rate; and adjusting the adjustable shunt valve by the user to change an opening valve pressure of the adjustable shunt valve to change the CSF flow rate to a desired CSF flow rate.

An apparatus for determining cerebrospinal fluid (CSF) flow rate in an implanted CSF shunt is disclosed. The apparatus comprises: a pad that is placed against the skin of a patient over the location of the CSF shunt, and wherein the pad comprises: a first plurality of temperature sensors (e.g., thermistors) that are aligned in a transverse direction with respect to the CSF shunt and wherein one of the first plurality of temperature sensors is aligned with the CSF shunt; and at least one temperature sensor associated with a temperature source (e.g., a Peltier device) that is positioned over the CSF shunt whenever the pad is placed against the skin and wherein the temperature source is applied continuously (e.g., 5 minutes or more) against the skin; and a sensor processing device that is electrically coupled to the pad for receiving temperature data from each of said temperature sensors during the continuous application of the temperature source, and for determining a flow rate of the CSF through the CSF shunt from the temperature data.

A method for determining cerebrospinal fluid (CSF) flow rate in an implanted CSF shunt is disclosed. The method comprises: applying a first plurality of temperature sensors against the skin over the location of the CSF shunt and wherein only one of the first plurality of temperature sensors is aligned with the CSF shunt; associating at least one temperature sensor with a temperature source (e.g., a Peltier device); activating the temperature source against the skin continuously and aligned with the CSF shunt, wherein the activating the temperature source comprises applying a temperature to the skin continuously (e.g., 5 minutes or more) that is different from a skin temperature; collecting temperature data from the temperature sensors during the continuous activation of the temperature source; and determining a flow rate of the CSF through the CSF shunt from the temperature data.

BRIEF DESCRIPTION OF SEVERAL VIEWS OF THE DRAWINGS

The invention will be described in conjunction with the following drawings in which like reference numerals designate like elements and wherein.

DETAILED DESCRIPTION OF THE INVENTION

The present invention 20 overcomes the deficiencies of the prior art by providing a system of thermosensors strategically placed on the skin surface and a cooling system. In particular, the present invention 20 provides a CSF real time, thermal flow measurement method and system which are capable of compensating for changing thermal properties of the skin and which are also capable of compensating for skin thickness (e.g., depth of shunt tubing implantation). The present invention 20 also provides a method of CSF real time, thermal flow measurement system which is based on three sets (arrays) of sensors and a cooling device. In addition, the present invention 20 also provides a method of shunt valve adjustment based on information provided by the CSF flow measuring system. Moreover, the present invention 20 provides a method of ICP assessment based on information provided by the CSF flow measuring system and settings of the adjustable shunt valve.

This invention 20 (see FIGS. 1 and 3) is the first rapid and non-invasive method for determining CSF flow rate through shunts in hydrocephalus patients. This invention 20 is an improvement upon ShuntCheck technology. The term "ShuntCheck" is a term used by the Assignee, namely, NeuroDx Development LLC, to identify the configuration of its apparatus that detects CSF shunt flow using a sensor patch 320 applied to the skin 301 of the patient and disposed over the implanted CSF shunt 310 and an associated CSF analyzer 400 that collects the data from the sensors on the sensor patch and either analyzes this data directly to provide CSF flow results or transmits such data to another device for CSF flow analysis.

Figure 6:
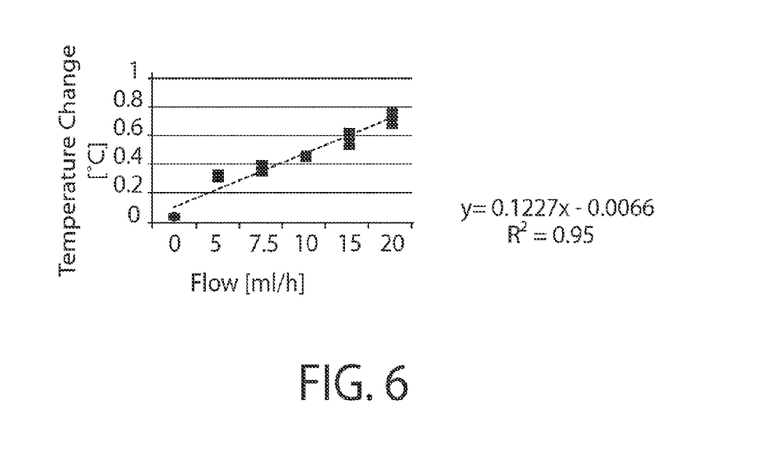
FIG. 6 ShuntCheck temperature dip vs flow rate for subcutaneous shunt in a porcine model.
Figure 7:
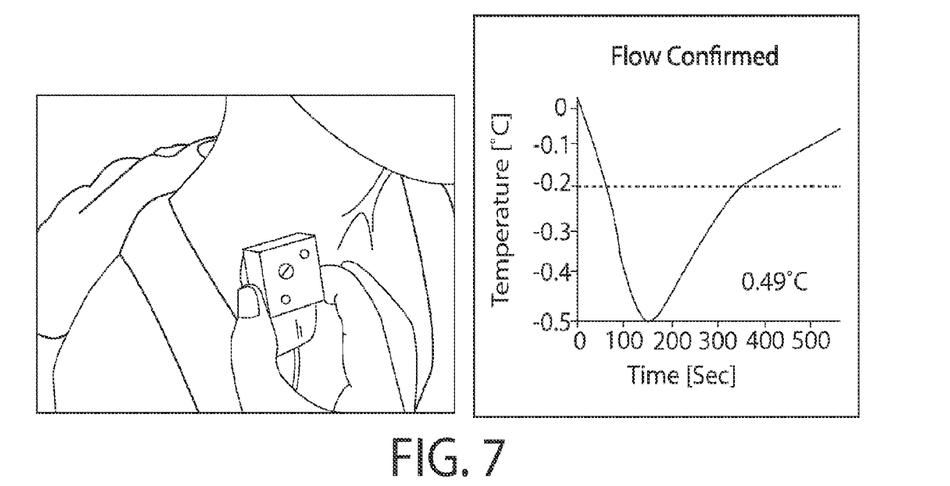
FIG. 7 is an illustration of ShuntCheck procedure (ice application) and the resulting temperature graph with corresponding bivariate output (in this case: flow confirmed)

The existing ShuntCheck FDA 510 k cleared device (see U.S. application Ser. No. 12/936,162 filed Oct. 1, 2010, entitled "Cerebrospinal Fluid Evaluation System Having Thermal Flow and Flow Rate Measurement Pad Using a Plurality of Control Sensors" is incorporated by reference in its entirety herein) is the starting platform for developing a novel system capable of determining absolute flow rate of fluid through a subcutaneous shunt. The platform consists of a single-use disposable thermosensor and a PDA based handheld device 400 (FIG. 3) that analyzes temperature-time data to provide a bivariate "flow" or "no-flow" result (FIG. 7). Ice applied on skin over shunt upstream causes surface temperature change of skin downstream, thereby indicating CSF flow inside. The thermosensor is an adhesive patch with temperature sensors (thermistors, by way of example only, the thermistors may comprise the MA100 Catheter Assembly which has a thermal response time in still water of 2.0 seconds. Another exemplary thermistor is the GE NTC thermistor) that is placed on the skin where the shunt crosses the clavicle. Ice is placed on the skin over the shunt catheter and "upstream" of the thermistors to cool the CSF inside. The change in temperature is measured by the thermosensor as cooled fluid flows beneath its thermistors. In this first generation device, the presence or absence of fluid flow is interpreted by a threshold magnitude (≥0.2° C.) change in temperature over time. The basis for believing that the platform is capable of determining the flow rate of the shunt fluid is that data obtained in an animal model indicate that the magnitude of temperature change detected by ShuntCheck is correlated to the magnitude of the shunt flow rate (FIG. 6). The limitation of the method for determining absolute flow rate, which is solved in current invention, is that skin surface temperatures are related not only to flow rate of fluid in the shunt, but also to other factors which vary among patients:

TABLE 1

| Factors which can affect skin temperature readings | |
|---|---|
| Factors | solution |
| Shunt depth in skin | Method for determining and compensating for depth |
| Skin thermal conductivity, specific heat & density | Method for measuring & compensating for thermal properties |

Preliminary data indicate that the components of the thermal dilution data that are dependent upon skin thickness and thermal property variability can be identified and removed from the data analysis, leaving only results that are dependent upon fluid flow rate. This enables the development of "quantitative ShuntCheck", able to measure absolute flow rates (not relative flow rates) reliably from test to test and person to person.

Figure 10:
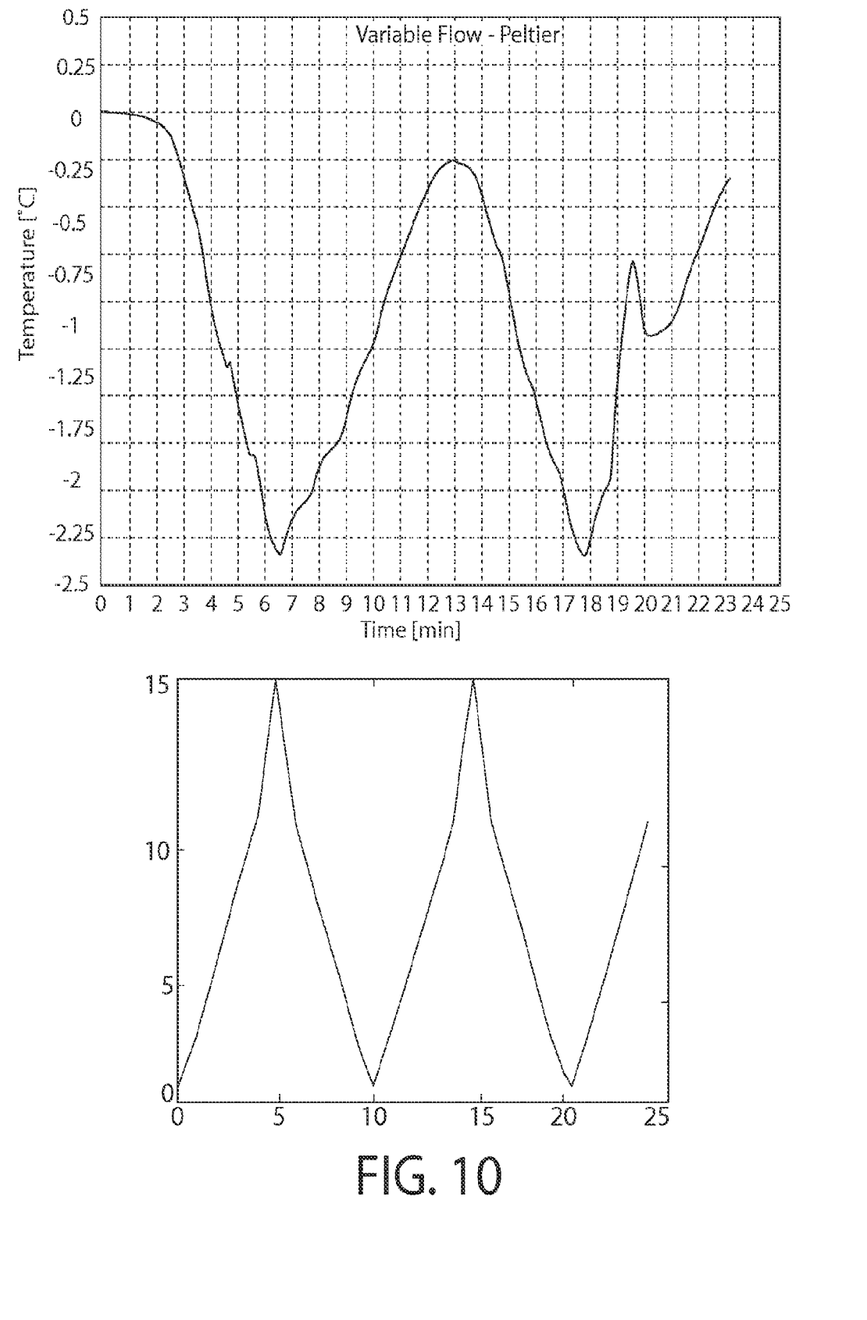
FIG. 10 includes a lower graph that shows true flow rates changing in time and an upper graph showing Peltier variable flow, temperature vs. time.

In addition, it has been determined that providing low level (safe for the skin tissue) constant cooling by a Peltier device (skin cooled down to about 20 Celsius) allows for long term real time measurements of CSF flow (see FIG. 10). The lower plot of FIG. 10 shows true flow rates in the shunt changing in time and the upper plot of FIG. 10 shows corresponding temperature output from a quantitative ShuntCheck device. It is clear that the thermal output corresponds closely to the simulated CSF flow in the shunt. Thus this method is suitable for real time monitoring of CSF flow.

This mode of operation is applicable for long term monitoring of patients, without necessity of repeated ice or other coolant application, by maintaining constant cold input to the system via the Peltier device and measuring CSF flow.

This feature combined with skin thickness compensation, and skin thermal properties assessment provides for long term, real time accurate CSF flow measurements.

Preliminary Data

There is a significant correlation between skin surface temperature change and shunt flow rate.

Thermal dilution data collected using the first generation ShuntCheck in an animal model indicate that the magnitude of temperature change detected by the thermosensors is highly correlated to flow rate (FIG. 6). A young porcine model was chosen as model because its skin is most similar to humans [22-27]. 7 Day old piglets (n=5) were implanted with a subcutaneous shunt through which warmed fluid (37° C.) was flowed at known rates using a volumetric pump. As flow rate was increased over the physiological range, the magnitude of the temperature change recorded by ShuntCheck increased linearly. The temperature change is calculated as a difference between the middle sensor 123 (FIG. 1) temperature and the average of two external sensors temperatures 122, 124 which are positioned against the skin 100 over the implanted shunt 110, which is at a skin depth, d (130). The same is true with regard to the second array of sensors 120, 121 and 125. This suggests that thermal dilution technology, which is now used only to determine the presence or absence of flow through the shunt, could be used to obtain absolute flow rates of fluid through a subcutaneous shunt if interpatient variability in factors other than flow rate that contribute to thermal dilution, such as skin thickness, thermal conductivity and diffusivity, can be measured.

Figure 1:
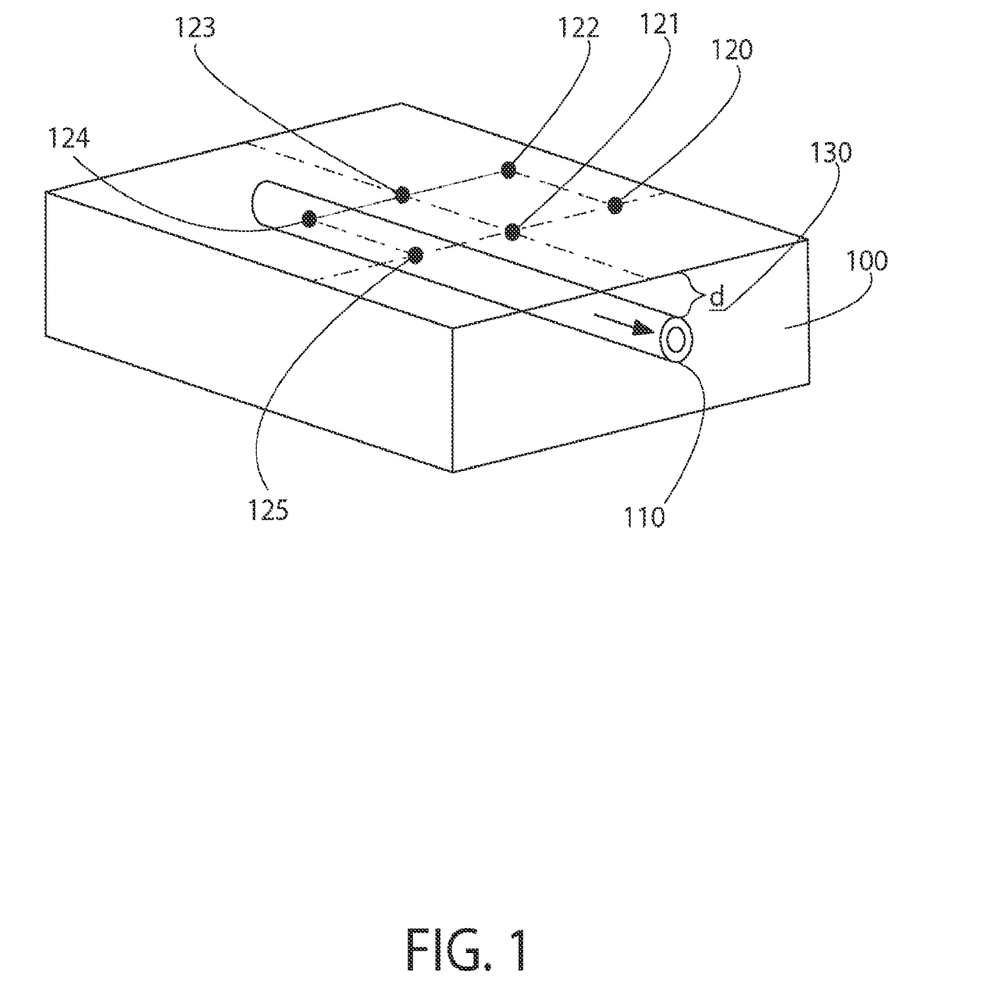
FIG. 1 is an illustration of a two sensor array configuration for CSF shunt flow measurements of the present invention and wherein the CSF shunt is implanted under the skin.
Figure 2:
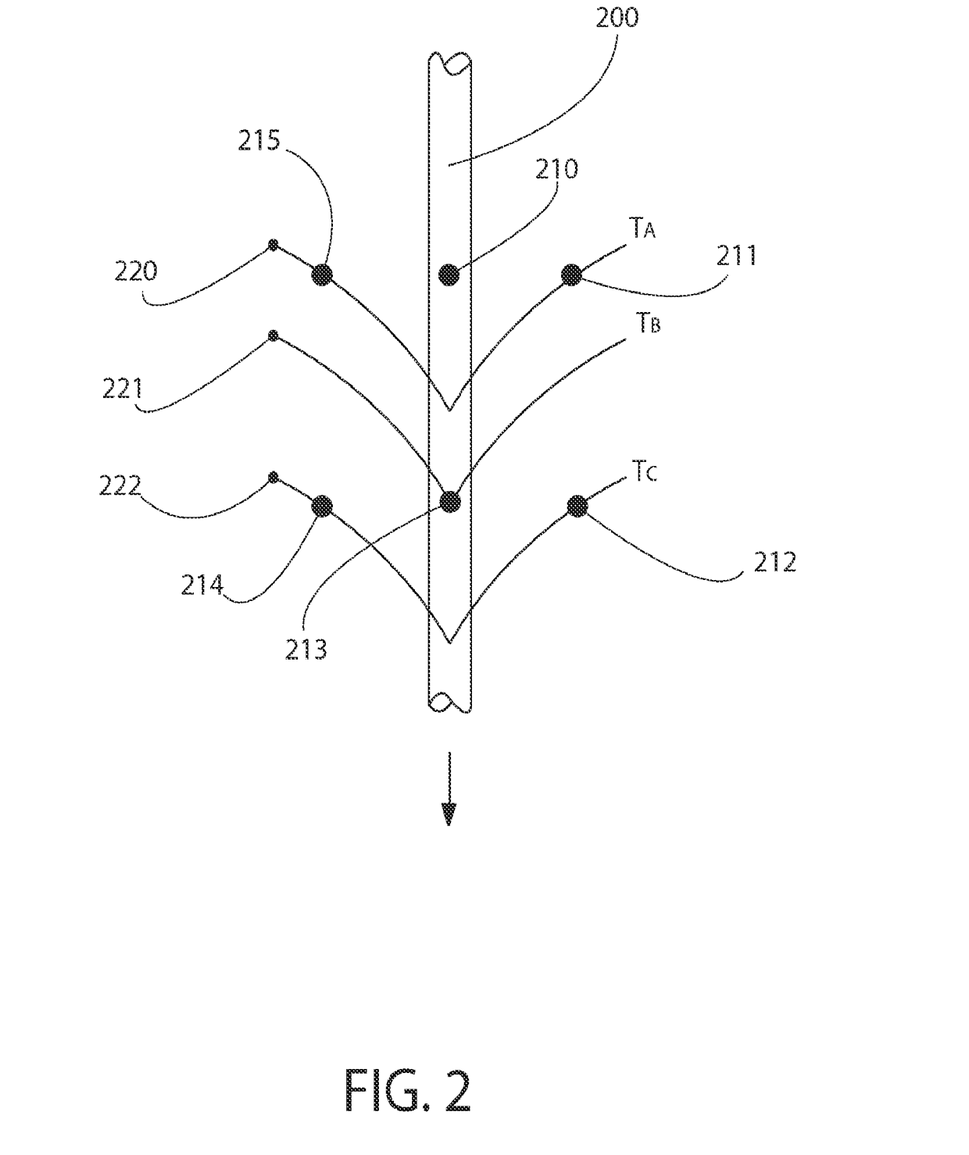
FIG. 2 is a top view of isotherms on the skin surface and temperature sensor distribution.

FIG. 2 provides a plan view of the sensor patch application site showing the temperature isotherms on the skin surface in relation to the position of the temperature sensors of FIG. 1. If the temperature source used upstream of the temperature sensors in FIG. 2 were, e.g., an ice cube, then isotherm $T_A$ would be the coldest detected temperature, isotherm $T_B$ would be slightly warmer and $T_C$ would be the warmest. Thus, references 215, 210 and 211 correspond to the positions of the temperature sensors 124, 123 and 122 respectively. Similarly, references 222, 213 and 212 correspond to the positions of the temperature sensors 125, 121 and 120, respectively.

T Prime (T') is Indicator for Skin Thickness Regardless of Flow Rate

Figure 8:
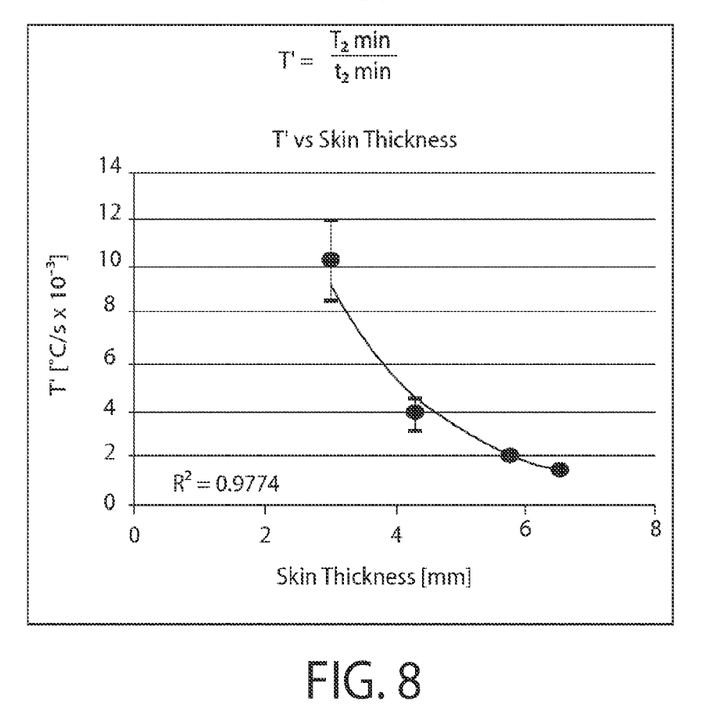
FIG. 8 is a graph showing T' vs depth of implantation (skin thickness overlaying the shunt) using four flow rates for each skin thickness.

A bench-top apparatus was created and validated to simulate our animal model—a heated body core (35 deg C.), covered by a silicon phantom skin with an implanted shunt (embedded in silicone) attached to a syringe pump so ShuntCheck tests could be run with known flow rates. Skin thickness of 3, 4, 6 and 7 mm were tested. As expected, we found that individual temperature changes detected on the "skin" overlying the shunt were influenced by the depth of the shunt. We next investigated various analysis techniques to identify the depth-dependent components of temperature measurement over the shunt. Two thermosensor arrays 321 and 322 (each consisting of three thermistors 330, 331, 332; and 333, 334 335, respectively, in a straight line perpendicular to the shunt so one sensor is over the shunt and two are adjacent for controls) were placed with a distance between them of 7 mm. A series of 16 ShuntCheck tests were run using four flow rates (5, 10, 15 & 20 ml/h) for each of the four skin thicknesses. We found that one analysis feature (which is referred to as T') was highly dependent upon skin thickness (FIG. 8), and less so upon flow rate. Therefore, when the thermal properties of tissue are known, the depth of shunt implantation can be determined. Once the depth of implantation is determined from T', an empirical formula for that particular skin thickness could be used to determine the flow rate. It should be noted that data points for several flows overlap. T' is a temperature gradient between two sensor arrays divided by the time needed to achieve maximum temperature dip on the first sensor array (inset) and wherein error bars represent 1 std error. This formula describes the relationship shown in FIG. 6 but calibrated to the particular skin thickness. Importantly, these data demonstrate that the depth of a shunt can be determined from surface temperature data, and eliminated from the analysis to (in part) enable absolute flow rates to be determined from thermal dilution data.

T' was calculated as ratio between the maximum temperature drop on the second array 321 and time needed for this maximum to occur. The temperature drop on the second array was calculated as temperature measured by sensor 331 minus the average of temperatures measured by sensors 330 and 332.

A Method for Determining the Thermal Properties of Skin for Each Test

Variability in skin conductivity (k), and diffusivity (α) are the final factors which must be compensated for in order to accurately measure flow rate of CSF in a shunt. To achieve this, we must find the effective k and α for each subject at the time of each quantitative flow rate test because they differ within and between subjects.

$$\nabla^2 T + \frac{q}{k} + \frac{1}{k} W_b C_b (T_b - T) = \frac{1}{\alpha} \frac{\partial T}{\partial t}$$

$$\nabla^2 T + \frac{q'}{k_{eff}} - \frac{q_{ice}}{k_{eff}} = \frac{1}{\alpha_{eff}} \frac{\partial T}{\partial t}$$

Figure 9:
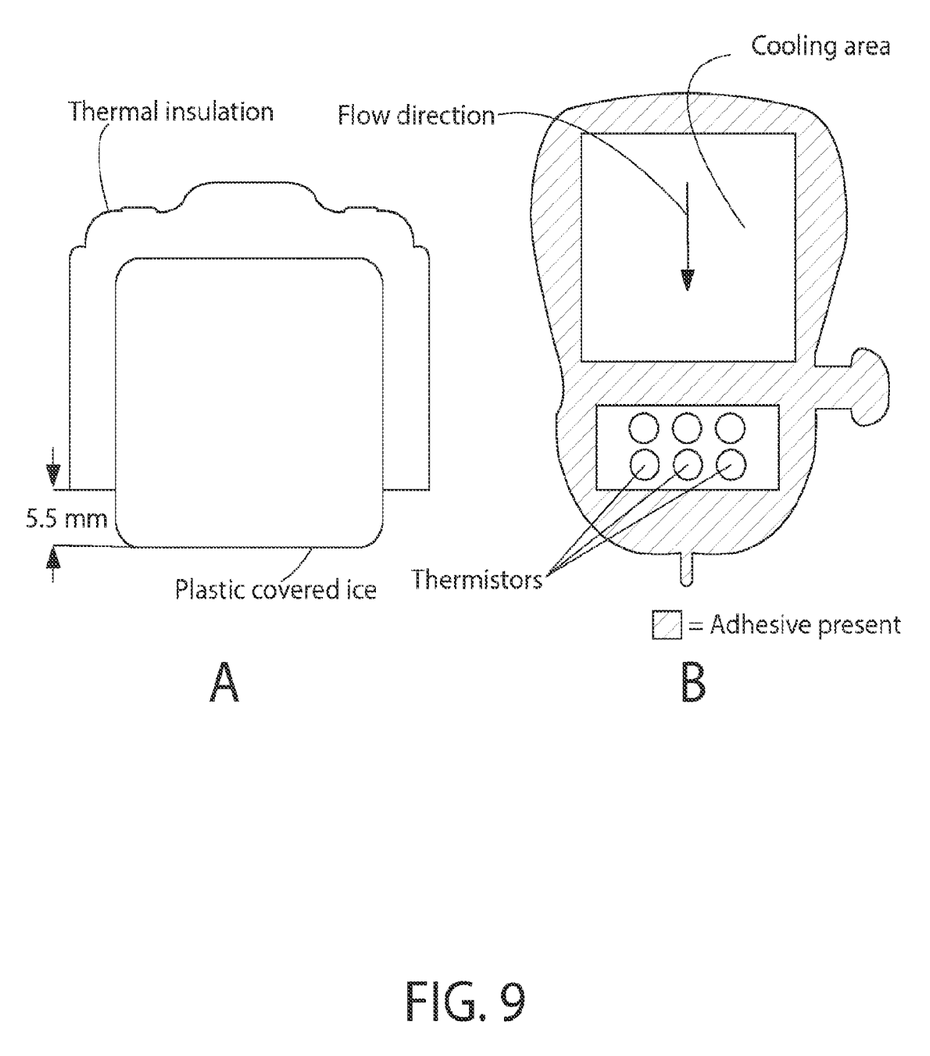
FIG. 9 is an illustration of the possible embodiment of the cooling apparatus and single array sensor of the present invention wherein panel A is a cross-section of the cooling apparatus which is a plastic-covered ice cube, and panel B is a bottom view of the sensing patch.

The Penne's bio-heat equation is shown above along with a reduced version that removes but accounts for perfusion via effective conductivity. The latter is commonly used in skin heat transfer problems, and requires $k_{eff}$ (effective skin conductivity) and $\alpha_{eff}$ (effective diffusivity) in order to solve for temperatures. Since those parameters are not known, the inverse problem must be solved where temperatures are used to determine them during each test. Each ShuntCheck test consistently removes a specific amount of energy from the system (skin and tissue) by cooling the skin surface with ice. The ice cube is a well defined cold source, isolated from the environment by a thermally insulating cup (see FIG. 9) and exposed only to skin, and with a known volume, specific heat and density. In particular, as shown in FIG. 9, panel A is a cross section of the cooling apparatus, a plastic covered ice cube in the thermal insulator. Tissue comes in contact with the ice cube at the bottom exposed side of the cube. By placing a thermistor inside this ice cube one can estimate q drained from tissue. Panel B of FIG. 9 shows the bottom view of the sensing patch with one array of thermal sensors measuring downstream temperature changes on the skin surface after cooling, this design is capable of measuring flow when d, k, c, and ρ are fixed. Adding one more array downstream allows for compensating for skin thickness, while adding another side array permits the measurement of thermal properties of tissue. By measuring the ice cube temperature one can estimate the amount of energy being absorbed by the ice cube. Under steady state conditions (which occurs in unshunted skin at about t=150 s; see FIG. 7), the temperature drop measured on the skin surface at a fixed distance will be proportional to skin conductivity and the amount of energy drained from tissue. When a thermosensor is placed on unshunted skin about 10 mm from where ice is applied for 60 sec, the temperature vs time cooling curve will reach a minimum, indicating a near steady state condition before it is re-warmed by autoregulation. Its shape is similar to the graph shown in FIG. 7 but with a shallower and flatter bottom since there would be no shunt or flow. The steady state heat transfer equation can then be solved for $k_{eff}$:

$$\frac{q}{\frac{dT}{dx}} Const = k_{eff}$$

where q is heat absorbed by the ice cube over a predefined period of time;

dT/dx is the temperature gradient registered by the sensor array at a point of steady state after 60 sec cooling; and Const is a constant specific to setup geometry which can be obtained by calibration with a material of known conductivity, k.

Effective diffusivity, $\alpha_{\mathit{eff}}$, can then be obtained by adding the time domain gradient measurement according the equation:

$$\frac{\partial^2 T}{\partial x^2} + \frac{\partial^2 T}{\partial y^2} + \frac{q}{k_{\mathit{eff}}} = \frac{1}{\alpha_{\mathit{eff}}} \frac{\partial T}{\partial t}$$

These methods enable all significant parameters needed for an accurate flow rate measurement to be determined for each ShuntCheck test. Once these values are known, the correct temperature vs time characteristic for the specific conductivity and diffusivity can be used to determine the flow rate, which is accurate because it accounts for the factors that vary in patients.

Figure 3:
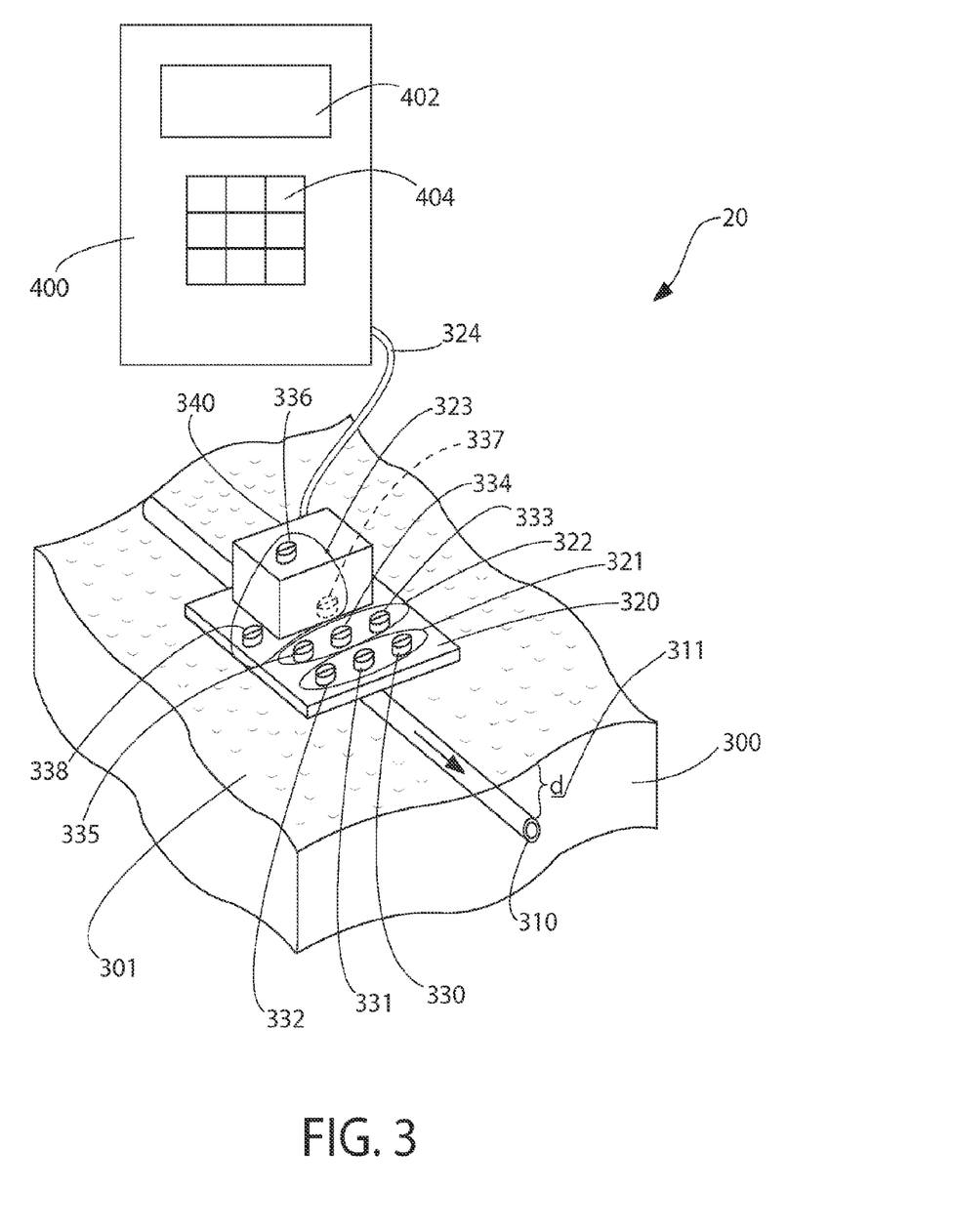
FIG. 3 is an illustration of the present invention depicting the sensor with a cooling-heating device positioned over the implanted CSF shunt.

In the preferred embodiment 20 there are three sensor arrays 321, 322, 323 as shown in FIG. 3. One sensor array 323 (comprising temperature sensors 336, 337 and 338, and also referred to as the "side array") collects data on cooling device 340 temperature, skin-cooling device interface 337, and skin 301 temperature (far from the shunt tubing 310). The second sensor array 322 (comprising temperature sensors 333, 334 and 335, also referred to as the "proximal array") and the third sensor array 321 (comprising temperature sensors 330, 331 and 332, also referred to as the "distal array") overlay the shunt tubing (FIG. 1, sensors 120, 121, 122, 123, 124). Those two arrays are responsible for measuring thermal changes related to CSF flow. The sensor arrays are attached to the skin surface 301 by an adhesive patch 320. In yet another embodiment they are attached by vacuum or adhesive paste (not shown). It should be understood that the second and third sensor arrays have their respective temperature sensors positioned on the surface of the sensor patch 320 that is placed against the skin 301. The same is true for sensors 337 and 338.

The preferred embodiment 20 comprises also a cooling-heating device 340 placed next to the sensor arrays 322, 320 and 323. The cooling-heating device 340 can be electronically powered and controlled (e.g. Peltier device). In another preferred embodiment it utilizes cold/warm media such as water, other fluid, ice (FIG. 9), dry ice, or cooling/warming spray. The cooling device cools down or heats up the skin surface 301, tissue 300 beneath the skin surface and section of the shunt tubing 310 (implanted at a skin depth d, or 311) with CSF fluid. The cooling-heating device is placed upstream or downstream of the second 322 and third 321 sensor arrays. The cooling device 340 is attached to the skin 301 via adhesive patch 320. In yet another embodiment it is attached by vacuum or adhesive paste not shown). The sensor array 323, used to calculate skin properties, is placed partially on the skin in location not overlaying the shunt tubing.

The downstream positioning of the cooling-heating device can best be understood considering whether there is CSF flow or no CSF flow. For example, in a situation where there is no CSF flow and the cooling-heating device (e.g., an ice cube) is positioned downstream of the distal array 321 (but not too far), cold temperature migrates in all directions from the position of the ice cube and part of that "cold migration" is detected by the distal array 321 and then the proximal array 322. Alternatively, if there is CSF flow and the ice cube is again placed downstream of the distal array 321 (but not too far), the temperature of the warm CSF flow warms the ice cube and this "warming migration" is detected by the distal array 321 and then the proximal array 322. Thus, locating the cooling-heating device downstream of the temperature sensor arrays is still an effective method of detecting CSF flow.

The system comprises also a reader-controller unit 400 (e.g., a CSF analyzer comprising a processor with 110) which collects data from all sensors (via a cable 340 or via a wireless configuration, not shown). The reader-controller unit 400 comprises a display 402 and keypad or other input mechanism 404. The reader-controller unit 400 can also control cooling-heating device 340 by increasing, decreasing or stabilizing 1) temperature or 2) heat generated or absorbed by the cooling device. The reader-controller unit 400 is capable of recording time stamps triggered by an operator or other external device. The time stamps indicate on the thermal data stream a precise point in time when the time stamp was triggered by an operator or an external machine. The reader-controller unit 400 also controls the activation of the temperature source 340 (e.g., Peltier device), as mentioned previously, either for heating or for cooling.

Figure 3A:
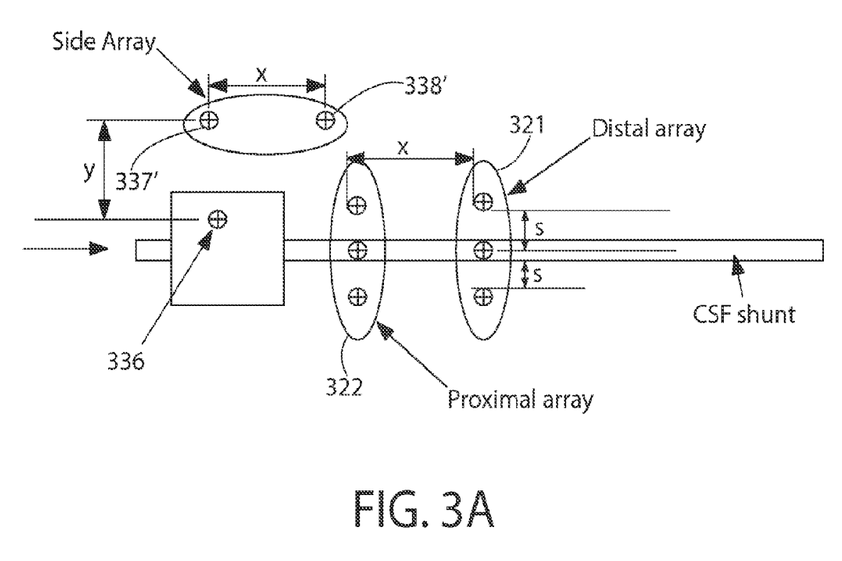
FIG. 3A is a top view of a configuration similar to FIG. 3 but showing the temperature sensors associated with the cooling-heating device in a slightly different orientation.
Figure 4:
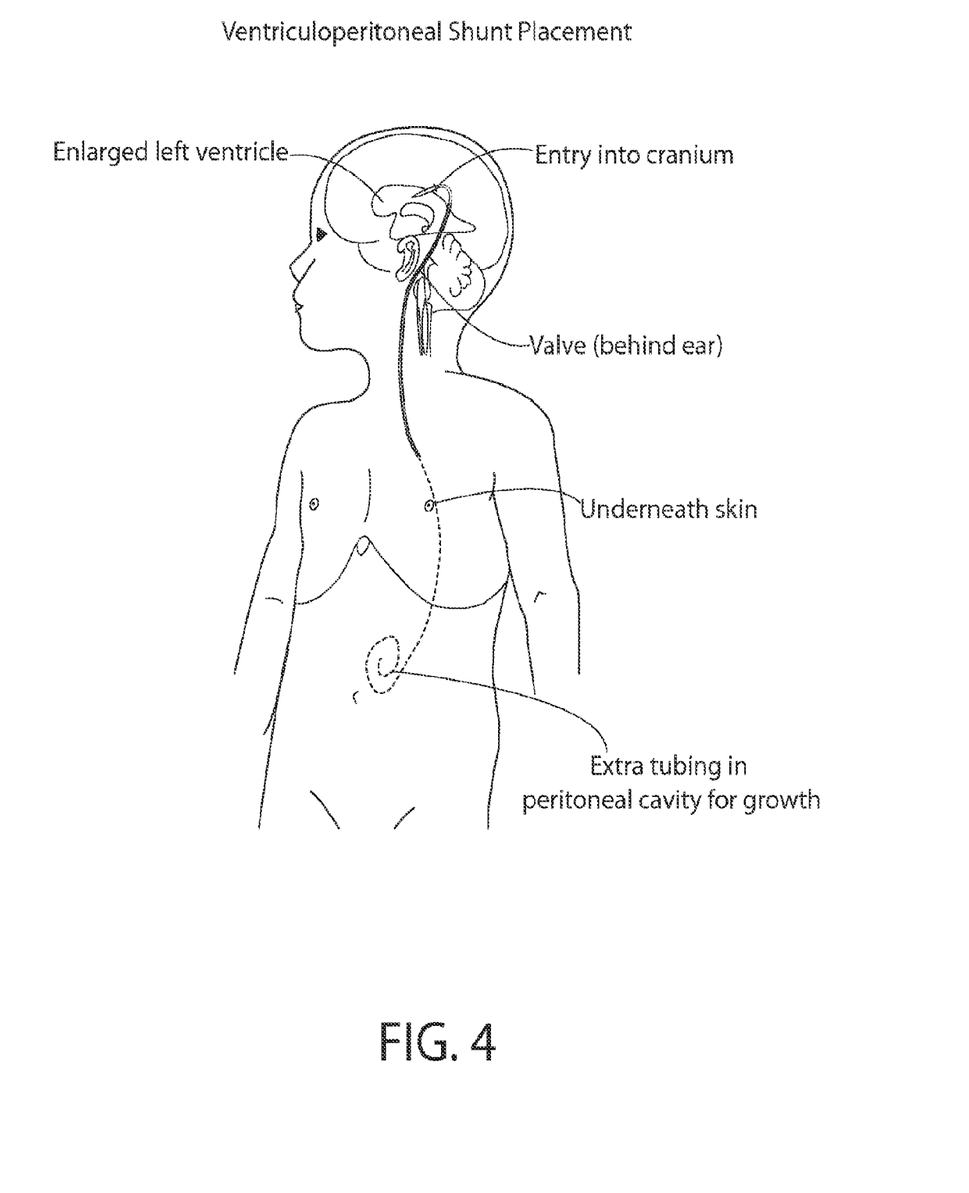
FIG. 4 is an illustration of ventriculoperitoneal shunt placement.
Figure 5:
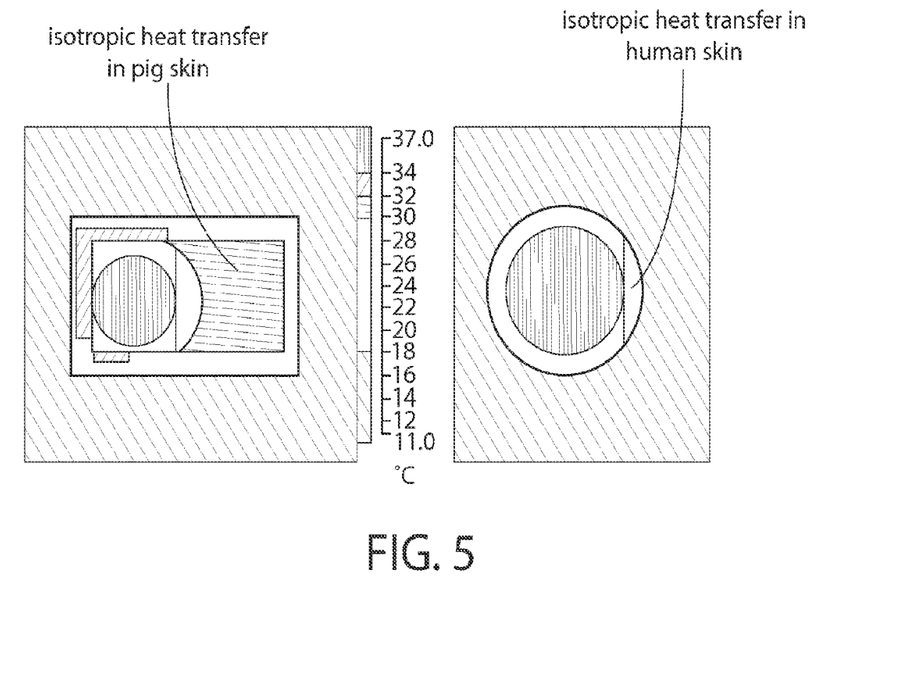
FIG. 5 is an illustration of isotherms after ice cube removal from the skin wherein the left panel shows isotropic heat transfer in animal (viz., pig) skin and the right panel shows isotropic heat transfer in human skin. It should be noted that there is no shunt underneath the two skins and the isotherms show no "triangular" shape as is shown in FIG. 2.

FIG. 3A is an illustration showing metrological configuration of the sensor patch necessary to accomplish skin depth and thermal properties compensation with real time multi-point measurement. In particular, FIG. 3A is a top view of a configuration similar to FIG. 3 but showing the temperature sensors associated with the cooling-heating device in a slightly different orientation. In particular, the sensors 337 and 338 are shown as sensors 337' and 338' aligned along an x-axis that is parallel to the CSF shunt and they are displaced away from the CSF shunt along a perpendicular axis, i.e., y-axis. As can also be seen from FIG. 3A, each of the sensors in the arrays 322 and 321 are aligned in a direction parallel to the CSF shunt. Furthermore, in each array the two outer or "control" sensors (i.e., 333/335 in array 322 and 332/330 in array 321) are displaced symmetrically ("s") along the y-axis from the CSF shunt.

The method(s) for actually calculating the CSF flow rate is discussed below and the terms T1, T2 and T3 refer to the temperature (T1) sensed by the central temperature sensors (e.g., 334 and 331) located over the shunt, the temperature (T2) sensed by the "right" control sensors (e.g., 333 and 330) and the temperature (T3) sensed by the "left" control sensors (e.g., 335 and 332).

It should be understood that the temperature source 340 could be either a cooling device or a heating device.

Calculating Flow Rate

In general, this method requires a lookup table(s) which has to be built experimentally for each model. The lookup table facilitates finding constants A, B, C, etc., used in model equations (see below). Then, the equation is used to calculate the flow rate (F).

1. Determine thermal conductivity $k_{\mathit{eff}}$ (as described previously)
2. Determine thermal diffusivity $\alpha_{\mathit{eff}}$ (as described previously)
3. Determine shunt depth (T' parameter)
The temperature source 340 (e.g., cooling device) has to be activated for a short period of time (e.g. 60 sec) and then turned off. During this period (during cooling and several minutes after) the temperatures on the two arrays 321 and 322 are measured.
4. Calculate the flow rate. The following calculations provide several options for calculating absolute flow rate:
Option 1: Calculate flow using a linear approximation (this solution works best for low flow rates of e.g., 0-20 ml/h)
With α, k and T' known, go to the look up table and find corresponding constants A, B;

Calculate flow (F) using A and B and the linear equation:

$$F = A*[T1-(T2+T3)/2]+B, \text{ using T1, T2 and T3 from any array 321 or 322.}$$

Option 2: Calculate flow using a polynomial approximation (this solution works best for extended range or flows of e.g., 0-60 ml/h)

With α, k and T' known, go to the look up table and find corresponding constants A, B, C, D, and E and calculate the flow (F) using:

$$F = A*[T1-(T2+T3)/2]\hat{}4 + B*[T1-(T2+T3)/2]\hat{}3 + C*[T1-(T2+T3)/2]\hat{}2 + D*[T1-(T2+T3)/2]+E,$$
using T1, T2 and T3 from any array 321 or 322.

Option 3A: Exponential Approximation

With α, k and T' known, go to the look up table and find corresponding constants A, B and C using the following exponential approximation:

$$F = A\hat{}[(B*(T1-(T2+T3)/2))]+C, \text{ using T1, T2 and T3}$$

(e.g. 333, 334, 335, FIG. 3) from any array 321 or 322. Temperature sensors have to belong to the same array (similar to the traditional ShuntCheck configuration).

Option 3B: Exponential Approximation

With α, k and T' known, go to the look up table and A', B' and C' and calculate flow from:

F=A'A^[(B'*(τ)]+C') where τ is the temperature difference between any pair of temperature sensors (e.g., thermistors) placed over the shunt tubing (e.g., 334 and 331 for T1) and so, in this case, the temperature sensors don't have to belong to the same array.

It should be understood that the reader-control unit 400 comprises a microprocessor or microcontroller that can employ these various calculations on the received temperature sensors' data or it can transmit the temperature sensors' data remotely (by cable or wirelessly) where the flow calculation is conducted and outputted (visibly for display or audibly).

It should be understood that the present invention can determine relative CSF flow (e.g., no flow, increased flow, decreased flow, etc.) or absolute CSF flow ("z" ml/h). As discussed previously, to determine absolute CSF flow, the parameters of skin thickness T', $k_{eff}$ (effective skin conductivity) and $\alpha_{eff}$ (effective diffusivity) must first be determined and then the temperature data from the various temperature sensor arrays analyzed.

To determine relative CSF flow, it is not necessary to first determine these three parameters; instead, the temperature data from the temperature sensor arrays can be analyzed and a relative flow can be determined from the equations involving T1, T2 and T3 discussed above. As mentioned previously, U.S. application Ser. No. 12/936,162 filed Oct. 1, 2010, entitled "Cerebrospinal Fluid Evaluation System Having Thermal Flow and Flow Rate Measurement Pad Using a Plurality of Control Sensors (whose entire disclosure is incorporated by reference herein) discloses a similar process. However, unlike application Ser. No. 12/936,162, the present invention 20 employs the controllable temperature source 340 that applies a given temperature for continuous period of time, rather than a short or abrupt pulse of temperature as disclosed in application Ser. No. 12/936,162. For example, where an ice cube is applied in application Ser. No. 12/936,162 for a short period of time (e.g., 60 seconds) and then removed, in the present invention 20, the temperature source 340 (e.g., a Peltier device) applies a substantially smaller temperature step to the skin of the patient and for a continuous period of time (e.g., 1 hour, 5 hours, 10 hours, 24 hours, etc.). Thus, the term "continuous" as used in this Specification implies a substantial period of time that is for more than 5 minutes. Moreover, in application Ser. No. 12/936,162, the temperature sensors collect data once the temperature source (e.g., the ice cube) is removed whereas in the present invention, the temperature sensor arrays are continuously collecting temperature data while the temperature source 340 is active. To accomplish this, the temperature source 340 applies a temperature magnitude that can be detected by the temperature sensor arrays but which is not uncomfortable to the patient since the temperature source 340 (e.g., the Peltier device) is applying this temperature for a continuous period of time. So, for example, the Peltier device 340 can be programmed, or controlled by the reader-controller unit 400, to apply a temperature to the skin that is 7°-14° C. lower than the skin temperature. Such a temperature difference is sufficient for the temperature sensors to detect the "cold" bolus in the CSF flow in the CSF shunt but yet which is not uncomfortable to the patient during the testing. Furthermore, in determining such relative flow, the use of a second array of temperature sensors is not required; hence, relative flow can be determined with either sensor array 322 or 321. In addition, this relative flow determination can also be achieved via the use of only one temperature sensor associated with the temperature source 340; for example, a temperature sensor (e.g., 336) placed on the temperature source 340 or a temperature sensor (e.g., 337) placed between it and the skin would be sufficient to determine relative flow.

Determining Intracranial Pressure (ICP) or Setting CSF Flow Using ShuntCheck

Figure 11:
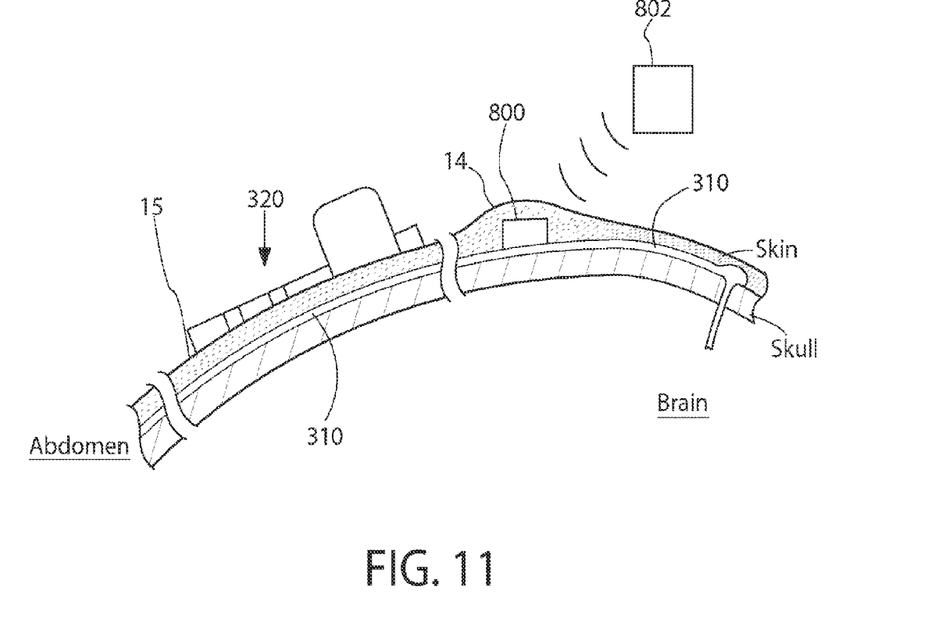
FIG. 11 shows a partial cross-sectional view of a patient' skull and clavicle showing the implanted shunt and adjustable shunt valve and wherein the ShuntCheck device is disposed on the skin surface at the clavicle.

The system can also be used along with adjustable (programmable) valves such as "Codman Hakim programmable valve" in order to assess patient's ICP. As shown in FIG. 11 by way of example only, an adjustable CSF shunt valve 800 forms part of the implanted CSF shunt 310 and the valve 800 is typically located behind the ear 14 of the patient. Thus, this valve 800 is located well upstream of where the sensor patch 320 is positioned (e.g., typically over the clavicle 15 of the patient (as also shown in FIG. 7) during use. Details of two such methods are described below:

The method of ICP assessment is claimed. Because the "opening pressure" of the adjustable shunt valve is a known parameter (e.g., 12 cmH$_2$O), this method can be utilized if there is no natural CSF flow in the shunt. The operator takes following steps 1) continuously observes flow measured by the ShuntCheck device; and 2) simultaneously decreases opening pressure of the CSF shunt valve; the shunt valve opening pressure can be controlled by an operator using a remote control 802 (e.g., via magnetic coupling), as shown in FIG. 11. The moment when ShuntCheck detects CSF flow, it is correlated with opening pressure of the valve 800, i.e., the opening pressure of the adjustable shunt valve 800 coincides with first CSF flow detection and thus this identifies the ICP. The operator of the remote control 802 is provided with a display, dial or other output mechanism (e.g., audible clicking, etc.) that indicates the current setting of the opening pressure of the adjustable shunt valve 800.

The method is claimed of using the system, when there is CSF flow in the shunt, in such a way that the operator 1) continuously observes CSF flow measured by the ShuntCheck device and 2) simultaneously the operator increases the opening pressure of the adjustable shunt valve (again, using the remote controller). The moment when ShuntCheck observes that there is no longer any CSF flow, again, this correlates with opening pressure of the valve. The opening pressure of the adjustable shunt valve coincides with the first "no-flow" detection and is then equal to ICP.

Similarly, this ShuntCheck device and adjustable shunt valve configuration can be used to obtain a desired CSF flow. In particular, the method is claimed of using this configuration in the following manner. If there is no CSF flow in the CSF shunt, the physician may make a determination based on the patient's age, weight, size, and/or other parameters, that a certain CSF flow should be present. The physician would monitor the ShuntCheck device as he/she used the remote control 802 to decrease the opening pressure of the valve 800 until the desired CSF flow is displayed on the ShuntCheck device at which time the physician would stop adjusting the valve. Conversely, if the patient were suffering from "overdrainage" (i.e., too much CSF flow whereby negative pressure is generated in the cranium which could result in hemorrhaging), the physician would monitor the ShuntCheck device as he/she used the remote control 802 to increase the opening pressure of the valve 800 until the desired CSF flow is displayed on the ShuntCheck device at which time the physician would stop adjusting the valve 800.

While the invention has been described in detail and with reference to specific examples thereof, it will be apparent to one skilled in the art that various changes and modifications can be made therein without departing from the spirit and scope thereof.

REFERENCES CITED

1. Bondurant, C. and D. Jiminez, Epidemiology of cerebrospinal fluid shunting. Pediatr Neurosurg, 1995. 23: p. 254-258.
2. Bech-Azeddine, R., et al., Idiopathic normal-pressure hydrocephalus: evaluation and findings in a multidisciplinary memory clinic. Eur J Neurol, 2001. 8: p. 601-611.
3. Patwardhan, N., Implanted ventricular shunts in the United States: the billion dollar a year cost of hydrocephalus treatment. Neurosurgery, 2005. 56: p. 139-145.
4. Zorc, J., et al., Radiographic evaluation for suspected cerebrospinal fluid shunt obstruction. Pediatr Emerg Care, 2002. 18: p. 337-340.
5. Laurence, K. and S. Coates, The natural history of hydrocephalus. Arch Dis Child, 1962.37: p. 345-362.
6. Eckstein, H. and G. Macnab, Myelomeningocoele and hydrocephalus: the impact of modern treatment. Lancet, 1966. i: p. 842-845.
7. Shurtleff, D., R. Kronmal, and E. Foltz, Follow-up comparison of hydrocephalus with and without meningocoele. J Neurosurg, 1975. 42: p. 61-68.
8. McCullough, D. and L. Balzer-Martin, Current prognosis in overt neonatal hydrocephalus. J Neurosurg, 1982. 57: p. 378-383.
9. Iskandar, B., et al., Pitfalls in the diagnosis of ventricular shunt dysfunction: radiology reports and ventricular size. Pediatrics, 1998. 101: p. 1031-1036.
10. Forrest, D. and D. Cooper, Complications of ventriculo-atrial shunts. J Neurosurg, 1968.29: p. 506-512.
11. Amacher, A. and J. Wellington, Infantile hydrocephalus: Long-term results of surgical therapy. Child's Brain, 1984. 11: p. 217-229.
12. Staal, M., M. Meihuizen-de Regt, and J. Hess, Sudden death in hydrocephalic spina bifida aperta patients. Pediatr Neurosci, 1987. 13: p. 13-18.
13. O'Brien, M. and M. Harris, Long-term results in the treatment of hydrocephalus. Neurosurg Clin N Am, 1993. 4: p. 625-632.
14. Iskandar, B., et al., Death in shunted hydrocephalic children in the 1990s. Pediatr Neurosurg, 1998. 28: p. 173-176.
15. Drake, J., et al., Randomized trial of cerebrospinal fluid shunt valve design in pediatric hydrocephalus. Neurosurgery, 1998. 43: p. 294-305.
16. Kestle, J., et al., Lack of benefit of endoscopic ventriculoperitoneal shunt insertion: a multicenter randomized trial. J Neurosurg, 2003. 98: p. 284-290.
17. McGirt, M., et al., Shunt survival and etiology of failures. Pediatr Neurosurg, 2002. 36: p. 248-255.
18. Collins, P., A. Hockley, and D. Woollam, Surface ultrastructure of tissues occluding ventricular catheters. J Neurosurg, 1978. 48: p. 609-613.
19. Sainte-Rose, C., Shunt obstruction: A preventable complication? Pediatr Neurosurg, 1993. 19: p. 156-164.
20. Ventureyra, E. and M. Higgins, A new ventricular catheter for the prevention and treatment of proximal obstruction in cerebrospinal fluid shunts. Neurosurgery, 1994. 34: p. 924-926.
21. Piatt, J., Physical examination of patients with cerebrospinal fluid shunt: is there useful information in pumping the shunt? Pediatrics, 1992. 89: p. 470-473.
22. Eggleston, T., et al., Comparison of two porcine (Sus scrofa domestica) skin models for in vivo near-infrared laser exposure. Comp Med, 2000. 50: p. 391-397.
23. Cohen, M., Measurement of the thermal properties of human skin. J Invest Dermatol, 1977. 69: p. 333-338.
24. Pitteti R. 2007. Emergency department evaluation of ventricular shunt malfunction: is the shunt series really necessary? Pediatr. Emerg. Care 23: 137-141.
25. Sood S, Canady A I, Ham, S D. 2000. Evaluation of shunt malfunction using shunt site reservoir. Pediatr. Neurosurg. 32: 180-186.
26. Hidaka M, Matsumae M, Kaoru I. Tsugane R. Saito I, 1995. Dynamic measurement of the flow rate in cerebrospinal fluid shunts in hydrocephalic patients. Eur. J. Nucl. Med. 28: 888-893.
27. Drake J, Sainte-Rose C, DaSilva M, Hirsh J-F, 1991. Cerebrospinal Fluid Flow Dynamics in Children with External Ventricular Drains. Neurosurgery. 28:242-250.

What is claimed is:

1. An apparatus for determining cerebrospinal fluid (CSF) flow rate in an implanted CSF shunt, said apparatus comprising:
   a pad that is configured to be placed against the skin of a patient over the location of the CSF shunt, said pad comprising:
   a first plurality of temperature sensors that are configured to be aligned in a transverse direction with respect to said CSF shunt and wherein one of said first plurality of temperature sensors is configured to be aligned with the CSF shunt; and
   a second plurality of temperature sensors that are configured to be aligned in a transverse direction with respect to said CSF shunt, downstream of said first plurality of temperature sensors, and wherein one of said second plurality of temperature sensors is configured to be aligned with the CSF shunt; and
   a third plurality of temperature sensors associated with a temperature source that are configured to be positioned over the CSF shunt whenever said pad is placed against the skin; and
   a sensor processing device that is electrically coupled to said pad for receiving temperature data from each of said plurality of temperature sensors, said sensor processing device configured to use said temperature data to remove the effects of skin depth of CSF shunt implantation, skin thermal conductivity and skin thermal diffusivity from temperature data collected by said first, second and third pluralities of temperature sensors, and said sensor processing device further configured to determine a flow rate of said CSF through said CSF shunt when a temperature source is applied to said pad.

2. The apparatus of claim 1 wherein said sensor processing device is configured to remove the effects of skin depth of CSF shunt implantation by calculating a ratio of a maximum temperature drop detected by a second plurality of temperature sensors, located downstream of said first plurality of temperature sensors, and a time required for said maximum temperature drop to occur.

3. The apparatus of claim 2 wherein each of said first and second plurality of temperature sensors comprises temperature sensors configured to be located on either side of said implanted CSF shunt and wherein said sensor processing device is configured to subtract an averaged value of detected temperature values of said second and third temperature sensors of said second plurality of temperature sensors from a detected temperature value of said first temperature sensor of said second plurality of temperature sensors.

4. The apparatus of claim 2 wherein said sensor processing device is configured to detect a temperature of said temperature source over a predetermined period of time divided by a temperature value from a temperature sensor at a steady state location after said predetermined period of time.

5. The apparatus of claim 4 wherein said sensor processing device is configured to determine skin thermal diffusivity by adding a ratio of heat absorbed by said temperature source versus said skin thermal conductivity to second partial derivatives in orthogonal axes which form a time domain gradient.

6. The apparatus of claim 1 wherein said temperature source is configured to be positioned on said pad upstream of said first plurality of temperature sensors.

7. The apparatus of claim 1 wherein said temperature source is a Peltier device.

8. The apparatus of claim 7 wherein said Peltier device is an ice cube.

9. The apparatus of claim 7 wherein said Peltier device is a heating device.

10. The apparatus of claim 1 wherein said pad comprises an adhesive for securing to the skin.

11. The apparatus of claim 1 wherein said pad is configured to use a vacuum for securing to said skin.

12. The apparatus of claim 1 wherein each of said temperature sensors is a thermistor.

13. A method for determining cerebrospinal fluid (CSF) flow rate in an implanted CSF shunt, said method comprising:
applying a first plurality of temperature sensors against the skin over the location of the CSF shunt and wherein only one of said first plurality of temperature sensors is aligned with the CSF shunt;
applying a second plurality of temperature sensors against the skin over the location of the CSF shunt, downstream of said first plurality of temperature sensors, and wherein only one of said second plurality of temperature sensors is aligned with the CSF shunt;
associating a third plurality of temperature sensors with a temperature source, said temperature source being applied against the skin aligned with the CSF shunt;
collecting temperature data from said first, second and third plurality of temperature sensors after a predetermined period of time has elapsed;
removing the effects of skin depth of CSF shunt implantation, skin thermal conductivity and skin thermal diffusivity; and
determining a flow rate of the CSF through the CSF shunt from said resultant temperature signal.

14. The method of claim 13 wherein said step of removing the effects comprises using said third plurality of temperature sensors to remove the effects of skin depth of CSF shunt implantation, skin thermal conductivity and skin thermal diffusivity from said collected temperature data.

15. The method of claim 14 wherein said step of removing the effects of skin depth of CSF shunt implantation comprises calculating a ratio of a maximum temperature drop detected by a second plurality of temperature sensors, located downstream of said first plurality of temperature sensors, and a time required for said maximum temperature drop to occur.

16. The method of claim 15 wherein said maximum temperature drop comprises:
arranging said second plurality of temperature sensors such that a first temperature sensor is located over said implanted CSF shunt and second and third temperature sensors are located on either side of said implanted CSF respectively; and
subtracting an averaged value of detected temperature values of said second and third temperature sensors from a detected temperature value of said first temperature sensor.

17. The method of claim 14 wherein said step of removing the effects of skin thermal conductivity comprises detecting a temperature of said temperature source over a predetermined period of time divided by a temperature value from a temperature sensor at a steady state location after said predetermined period of time.

18. The method of claim 17 wherein said skin thermal diffusivity is obtained by adding a ratio of heat absorbed by said temperature source versus said skin thermal conductivity to second partial derivatives in orthogonal axes which form a time domain gradient.

19. The method of claim 13 wherein said step of associating a third plurality of temperature sensors comprises said temperature source being applied upstream of said first plurality of temperature sensors.

20. The method of claim 13 wherein said step of associating a third plurality of temperature sensors comprises said temperature source being applied downstream of said second plurality of temperature sensors.

21. The method of claim 13 wherein said step of associating a third plurality of temperature sensors with a temperature source comprises associating a third plurality of temperature sensors with a Peltier device.

22. The method of claim 21 wherein said Peltier device is an ice cube.

23. The method of claim 22 wherein said Peltier device is a heating device.

24. The method of claim 13 wherein each of said plurality of sensors is adhesively secured to the skin.

25. The method of claim 13 wherein each of said plurality of sensors is secured by a vacuum to said skin.

26. The method of claim 13 wherein each of said temperature sensors is a thermistor.

* * * * *